United States Patent [19]
Broad, Jr.

[11] Patent Number: 5,829,440
[45] Date of Patent: Nov. 3, 1998

[54] CONTRACEPIVE DEVICE AND METHODS AND APPARATUS FOR ASSEMBLING THE SAME

[76] Inventor: Robert L. Broad, Jr., 2300 Brookwood Dr. SE., Decatur, Ala. 35601

[21] Appl. No.: 451,274

[22] Filed: May 30, 1995

Related U.S. Application Data

[63] Continuation-in-part of Ser. No. 300,140, Jan. 23, 1989, Pat. No. 4,972,850, and a continuation-in-part of Ser. No. 300, 139, Jan. 23, 1989, Pat. No. 4,987,905, and a continuation-in-part of Ser. No. 614,154, Nov. 16, 1990, Pat. No. 5,165, 422, and a continuation-in-part of Ser. No. 977,919, Nov. 18, 1992.

[51] Int. Cl.$^6$ ........................................................ A61F 6/02
[52] U.S. Cl. ........................... 128/842; 128/844; 128/918
[58] Field of Search ..................................... 128/842, 844, 128/918; 604/347, 353; 198/803.3, 803.1, 803.9; 206/69; 29/235

[56] References Cited

U.S. PATENT DOCUMENTS

| | | | |
|---|---|---|---|
| 2,285,981 | 6/1942 | Johns | 604/349 |
| 2,586,674 | 2/1952 | Lonne | 128/844 |
| 4,852,586 | 8/1989 | Haines | 128/844 |
| 4,934,382 | 6/1990 | Barone | 128/844 |
| 5,082,004 | 1/1992 | Reddy | 128/918 |

FOREIGN PATENT DOCUMENTS

9008522  8/1990  WIPO ..................................... 128/918

Primary Examiner—Michael A. Brown

[57] ABSTRACT

Methods and apparatus for assembling a contraceptive device made up of a rolled condom having an open end having a ring and a closed end having thereon a ribbed, inverted reservoir, with a pair of strips rolled into the condom on opposite sides thereof for unrolling the condom onto the penis. The condom in unrolled condition is placed on an elongated form and the ends of the strips are brought into contact with the condom and held there by streams of air. A pair of elongated rolling elements are brought into contact with the condom ring and moved in a direction parallel to the form to roll the condom and strips, the preferred rolling elements being in the form of a tube coaxial with the form. The form is provided with a recess in the end thereof for receiving the reservoir when a vacuum is applied to the recess. Intermediate portions of the strips are moved toward each other and held there as two heat-sealable packaging sheets are moved together on opposite sides of the condom, the free ends of the strips extending in opposite directions from the condom. Heat and pressure are applied to the packaging sheets around the edges thereof to seal the packaging sheets together to form a package, the ends of the strips being sealed to opposite sides of the package.

32 Claims, 6 Drawing Sheets

CONTRACEPIVE DEVICE AND METHODS AND APPARATUS FOR ASSEMBLING THE SAME

This application is a continuation-in-part application of: application Ser. No. 300,140, filed Jan. 23, 1989 (now U.S. Pat. No. 4,972,850); Ser. No. 300,139, filed Jan. 23, 1989 (now U.S. Pat. No. 4,987,905); Ser. No. 614,154, filed Nov. 16, 1990 (now U.S. Pat. No. 5,165,422); and Ser. No. 977,919, filed Nov. 18, 1992.

BACKGROUND

1. Field of the Invention

This invention relates to contraceptive devices and methods and apparatus for making them.

2. Prior Art

Condoms have been made for many years by dipping a form into a latex solution, withdrawing the form from the solution and then curing the layer of latex adhering to the form. The condom is then removed from the form by rolling it. During further processing and testing of the condom it may be placed on several different forms by unrolling it onto the form and then rolling it to remove it from the form.

The rolling and unrolling of a condom in a conventional condom plant is usually done by rotating brushes or rollers. Typically, a form carrying the condom is moved past a rotating brush or roller and the brush or roller rolls or unrolls the condom as the form carries it past the brush.

This application discloses a contraceptive device made up of a condom having a pair of strips rolled into the condom on opposite sides thereof for unrolling the condom onto the user's penis. The device is assembled by placing a condom on an elongated form, placing the pair of strips in contact with the condom on opposite sides thereof and then rolling the condom and, with it, the strips. The ends of the strips must be held in contact with the condom when the rolling is started or they will not be rolled into the condom and the device will be inoperative for its intended purpose.

A rotating brush or roller could be used to unroll the condom of this new contraceptive device onto the form but a brush cannot be used to roll the condom with the strips. The reason for this is that, after the strips have been placed on opposite sides of the condom on the form, the form must be moved to and past the rotating brush and there has been no way to keep the ends of the strips in contact with the condom until the brush is reached. The strips are very thin and have almost no weight, so that the slightest stirring of air in the room will move the feather-light strips away from the condom. The rotating brush will roll the condom but the strips will be hanging, loose, somewhere else and will not be rolled into the condom, thereby making the device inoperative for its intended purpose. This problem, which is more severe when wider strips are used, makes it impossible to use prior art methods and apparatus for assembling this new contraceptive device.

Further, condoms have been made the same way and have had the same problems and disadvantages for decades. Certain problems that have existed with condoms for over half a century still exist with condoms being sold today. One such problem is the fact that the condom user is admonished to squeeze the condom reservoir flat and hold it that way while the condom is being donned. The slippery lubricated condom is already difficult enough to put on without requiring an extra hand to hold the reservoir flat.

Conventional condoms are packaged by sandwiching the rolled condom between a pair of packaging sheets and then sealing the sheets to each other around the edges thereof. The use of wider strips for unrolling the condom results in several problems during the assembly and packaging of the device, which problems do not exist with conventional condoms without the strips or with narrow strips.

SUMMARY OF THE INVENTION

A contraceptive device made up of a rolled tubular condom having an open end and a closed end having thereon a ribbed, inverted reservoir, with a pair of strips of a preferred width being rolled into the condom on opposite sides thereof for unrolling it onto the penis. Methods and apparatus are provided for assembling the device wherein the condom is placed on an elongated form and the first ends of the strips are brought into contact with the condom and held on opposite sides thereof adjacent to the open end of the condom. Streams of air applied to the strip ends is the preferred way of holding the first ends of the strips in contact with the condom as elongated rolling elements are brought into contact with the condom at the open end thereof and then moved in directions parallel to the condom axis toward the closed end of the condom to roll the condom and the strips. Intermediate portions of the strips are moved radially inward toward each other by fingers or streams of air and held there as two heat-sealable packaging sheets are moved together on opposite sides of the rolled condom, with second ends of the strips extending away from the condom in opposite directions. A package is formed by applying heat and pressure to the packaging sheets to seal the sheets to each other in a zone extending around the periphery of the thereof, with dies being provided for applying differing amounts of heat to subzones making up the sealed zone.

DETAILED DESCRIPTION OF THE DRAWINGS

DETAILED DESCRIPTION OF THE INVENTION

The Device

Figure 1:
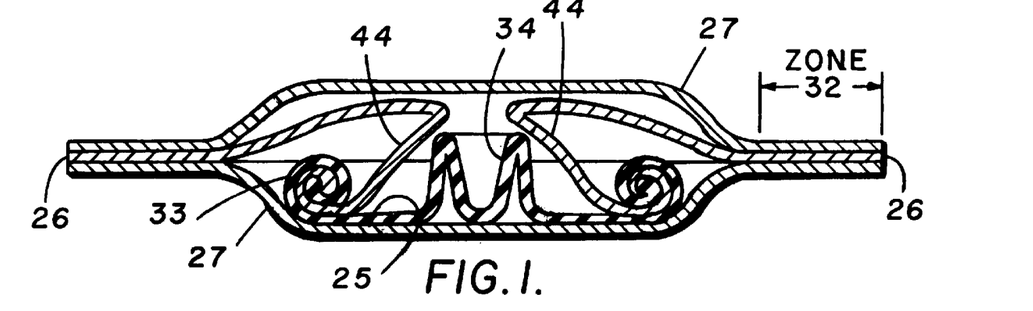
FIG. 1 is an enlarged cross sectional view of the device showing the parts of the device separated vertically for clarity.

Referring now in detail to the drawings, FIG. 1 shows a cross sectional view of the device with the various parts of the device separated vertically for clarity. The device is made up of a rolled condom 25 with a pair of strips 26 rolled into the condom on opposite sides thereof. The strips are preferably made of a thermoplastic material such as polyethylene, with a thickness of about 0.01 to 0.03 millimeters and preferably have widths such that the sum of the widths of the strips is at least 20% of the length of the circumference of the rolled condom. Narrow strips tend to allow the condom to prematurely unroll (i.e., unroll slightly before the condom contacts the penis), frequently resulting in a tangled condom which cannot be used. The condom is housed in a package made up of a pair of packaging sheets 27 which sandwich the condom 25 therebetween, with the sheets 27 being sealed to each other in a zone 32 extending around the peripheries of the sheets.

Figure 3:
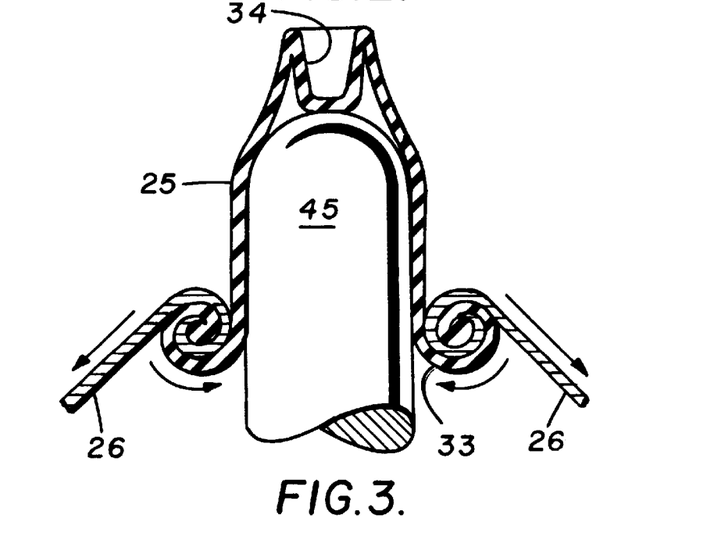
FIG. 3 is a cross sectional side view showing the manner in which the condom is unrolled onto the penis when the strips which are rolled into the condom are pulled.

The condom has a tubular configuration when unrolled, with a closed end and an open end with a ring 33 extending around the open end. The ring 33 may be the ring which extends around the open end of a fully unrolled conventional condom (FIG. 8) or it may be formed by a portion of the condom which has been rolled (FIG. 3). The closed end of the condom is provided with a generally cylindrical reservoir 34 which is inverted as shown in FIGS. 1 and 3.

The reservoir 34 is inverted at some point during the assembly of the device and that configuration is maintained during the packaging so that, when the package is opened, the reservoir will still be inverted By keeping the reservoir inverted, the necessity of squeezing the reservoir flat and holding it that way while the condom is being put on is obviated This makes it much easier to don the condom, since it frees up one hand. Preferably the condom is placed on a form (not shown) having in the end thereof a recess having a size sufficiently large to receive the reservoir. A vacuum is applied to the recess to invert the reservoir into the recess. This is a known process.

In order to insure that the reservoir maintains its inverted configuration, the reservoir 34 is provided with a group of ribs 38 (FIGS. 4 and 5) arranged in an annular zone extending around the periphery of the reservoir The ribs 38 are shown extending longitudinally along the reservoir but may extend in other directions so long as there is no annular band of the reservoir in the zone which is free of ribs.

Figure 4:
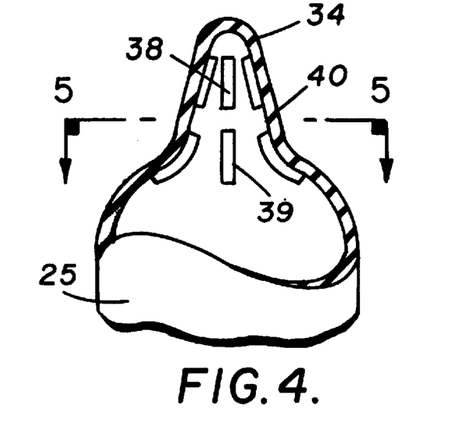
FIG. 4 is an enlarged, fragmentary cross sectional view of the closed end of the condom of this invention showing ribs which serve to maintain the condom reservoir in an inverted configuration.

Preferably, there is a second group of ribs 39 which are arranged in an annular band around the reservoir on the closed end of the condom 25 as shown in FIG. 4. This second group of ribs is longitudinally spaced from the first group to leave an annular band 40 between the zones which is free of ribs. The two spaced groups of ribs insure that, when the reservoir is inverted, the bending will occur in the rib-free band 40. This precisely controls the amount of reservoir which is inverted and significantly reduces the likelihood that the reservoir will lose its inverted configuration during further processing and packaging.

Figure 5:
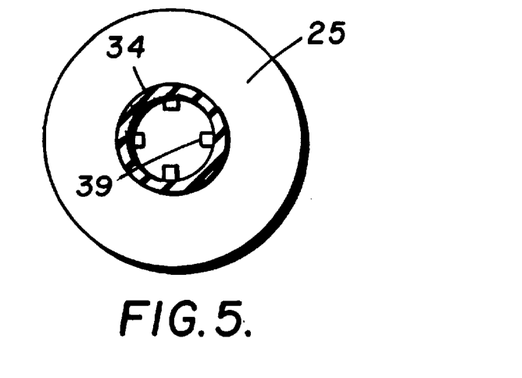
FIG. 5 is a cross sectional view taken on line 5—5 of FIG. 4 showing the ribs which maintain the reservoir in an inverted condition.

The ribs 38 and 39 may be in the form of corrugations but are preferably in the form of solid ribs as shown in FIGS. 4 and 5. The ribs 38 and 39 may be formed by providing the form on which the condom is to be made with slots or grooves (not shown) which will fill when the form is dipped into the latex solution. Upon curing, the ribs become a permanent part of the condom.

Figure 25:
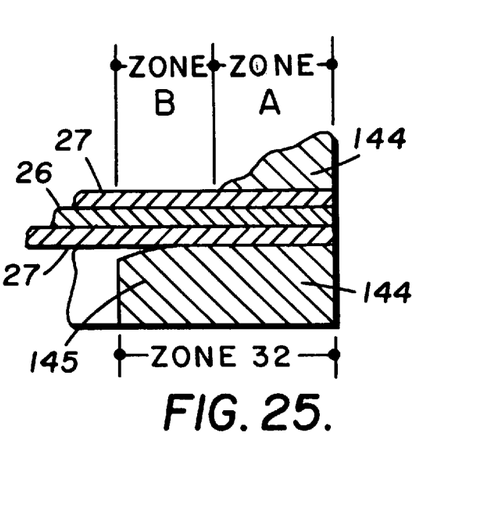
FIG. 25 is a cross sectional view taken on line 25—25 of FIG. 24 showing the cross sectional configuration of the dies which provide differential heating in that portion of the package which is sealed.

It can be seen that the ends of the strips 26 are sealed between the packaging sheets 27 at opposite edges of the package in the zone 32 (FIGS. 1 and 25). Intermediate portions 44 of the strips 26 are forced inward toward each other (as described below) prior to sealing the packaging sheets to provide slack in the strips. Without this slack, the condom cannot be pulled from the package (after the package is torn into two parts) without premature unrolling of the condom. If the condom unrolls prematurely (prior to contact with the penis) even a slight amount, part of the unrolled end of the condom is likely to become rolled into the unrolling condom and cause the condom to become tangled to the point where it cannot be used.

Figure 2:
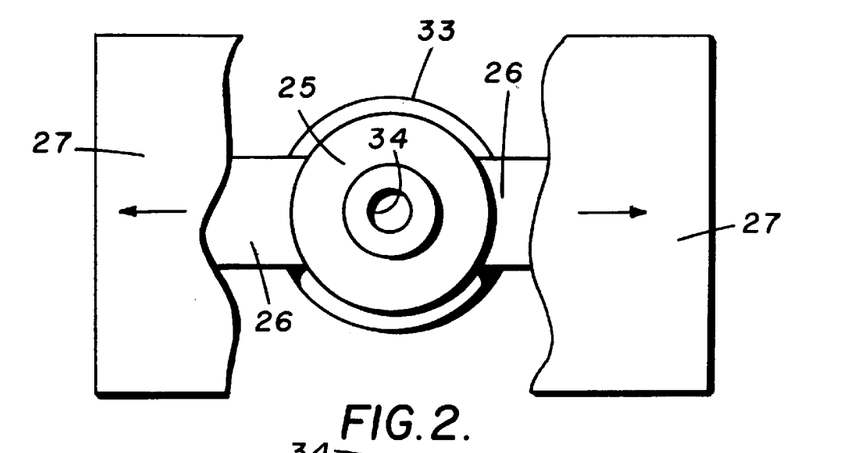
FIG. 2 is a plan view of the device showing the manner in which the condom is pulled out of the package after the package has been opened.

FIG. 2 shows the device after the user has opened the package. The user opens the package by tearing it into two generally equal parts. Holding the two parts of the package and moving them away from each other pulls the condom 25 out of the package and into the position shown in FIG. 2. Still holding the two parts of the package, the user moves the condom 25 into contact with the end of his penis 45 (FIG. 3) and then gives his wrists a quick flick. The condom 25 will instantly unroll onto the penis 45 as shown in FIG. 3 without the user touching it with his hands. Because of the ribs 38 and 39, the reservoir 34 will retain its inverted configuration as shown in FIG. 3, so that there is no need to squeeze the reservoir flat and hold it that way as the condom is being donned.

The methods and apparatus for assembling the device are described below.

Assembly of the Condom and Strips

Figure 6:
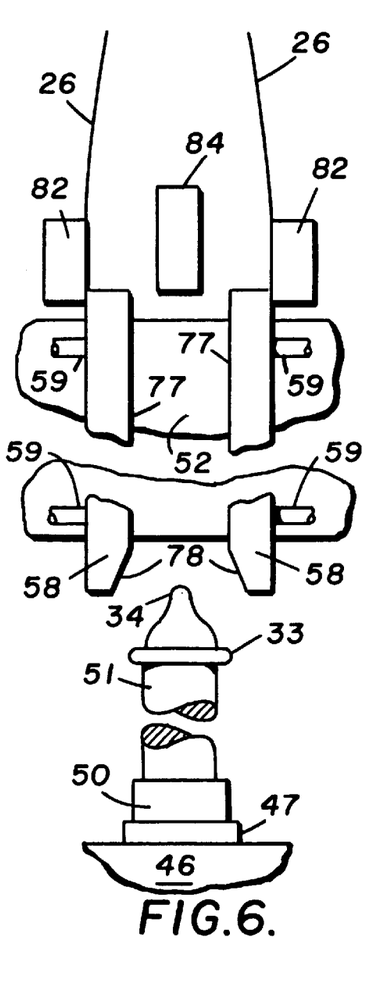
FIG. 6 is a schematic side view of apparatus used for assembling the device of this invention showing the apparatus in a first position at the start of a cycle of operation.

FIG. 6 is a schematic side view showing apparatus used for assembling the condom and strips. This apparatus includes a base 46 supporting a conveyor 47 carrying a plurality of blocks 50. Attached to and extending upward from each block 50 is a cylindrical form 51 having a proximal end secured to the block 50 and a free distal end, the distal end being rounded as shown in the drawings. The free end of the form 51 is preferably provided with the recess (not shown) described above.

Figure 12:
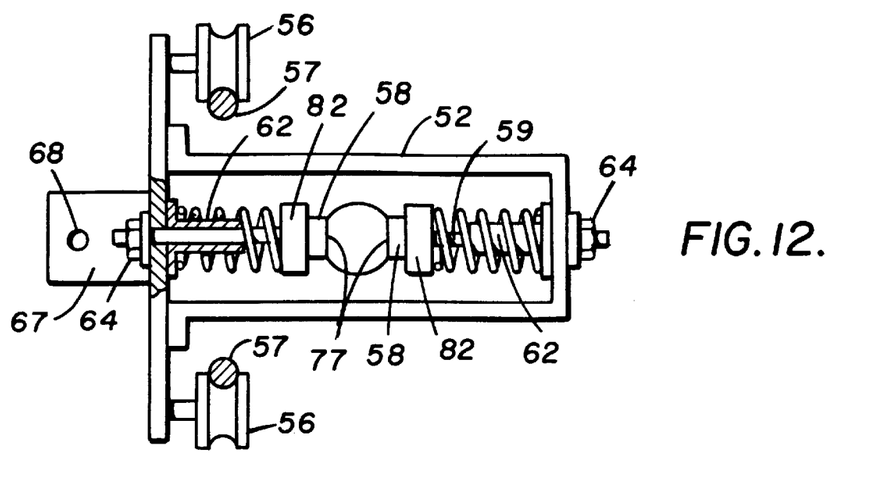
FIG. 12 is a plan view of a carriage which supports and moves elements which roll the condom showing how the rolling elements are supported.

A carriage 52 (FIG. 12) is provided with rollers 56 which roll along a pair of guide rods 57 which are attached to the base and extend vertically upward, parallel to each other, to serve as a track for the reciprocation of the carriage 52.

The carriage 52 carries a pair of elongated rolling elements 58 which are supported by rods 59 which are slidably mounted in tubular portions 62 secured to the carriage 52. Compression springs 63 (FIG. 12) urge the rolling elements 58 toward each other, with nuts 64 being threaded onto the ends of the rods 59 to adjust the innermost positions of the rolling elements and to center the rolling elements on the form 51 on opposite sides thereof. Each rolling element 58 is supported by a pair of rods 59, one positioned above the other. A bracket 67 attached to the carriage 52 is provided with a hole 68 for securing the carriage to a piston rod 69 of a cylinder 76 (FIG. 19) for moving the carriage up and down.

The purpose of the rolling elements 58 is to simultaneously unroll the condom 25 onto the form 51 and pull the strips into position to be rolled and then, after the strips 26 are in place, to roll the condom and the strips. The lower ends of the rolling elements 58 are provided with beveled surfaces 78 (FIGS. 6 and 11) which, upon downward movement, engage the ring 33 of the condom 25 and begin to unroll the condom onto the form 51 when the condom is positioned on the upper end of the form as shown in FIG. 6. Elongated rolling surfaces 77 extend from the beveled surfaces 78 along the rolling elements to continue unrolling the condom 25 onto the form 51 as the carriage 52 moves the rolling elements downward. It can be seen that the rolling surfaces 77 move along paths generally parallel to the axis of the form 51, with the carriage 52 supporting the rolling elements 58 in such a manner that the rolling elements 58 are free to move toward and away from the axis of the form as the diameter of the condom ring 33 changes as it is being rolled or unrolled.

FIG. 6 shows the apparatus at the beginning of a cycle of operation, with the rolling elements 58 being in a first position at this point. The ends of the strips 26 are held by feed or advance manifolds 82 attached to and carried by the rolling elements 58. The feed manifolds are hollow blocks which are provided with apertured faces 83 (FIG. 11) which face each other. By applying a negative air pressure to the hollow feed manifolds 82, air will be drawn into the manifold to pull the ends of the strips 26 against the apertured faces 83 and hold them there. It can be seen that, as the rolling elements 58 are moved downward to unroll the condom onto the form 51, the strips will be pulled downward to position them for rolling into the condom.

In this first position (FIG. 6), a holding manifold 84 (shown in detail in FIGS. 9 and 10) is positioned between the feed manifolds 82 carried by the rolling elements 58. The feed manifolds 82 hold the ends of the strips 26 during the first half of the apparatus operating cycle. The purpose of the holding manifold 84 is to hold the strips during the second half of the operating cycle after the strips have been severed and as the rolling elements 58 are being returned to the positions shown in FIG. 6.

Figure 13:
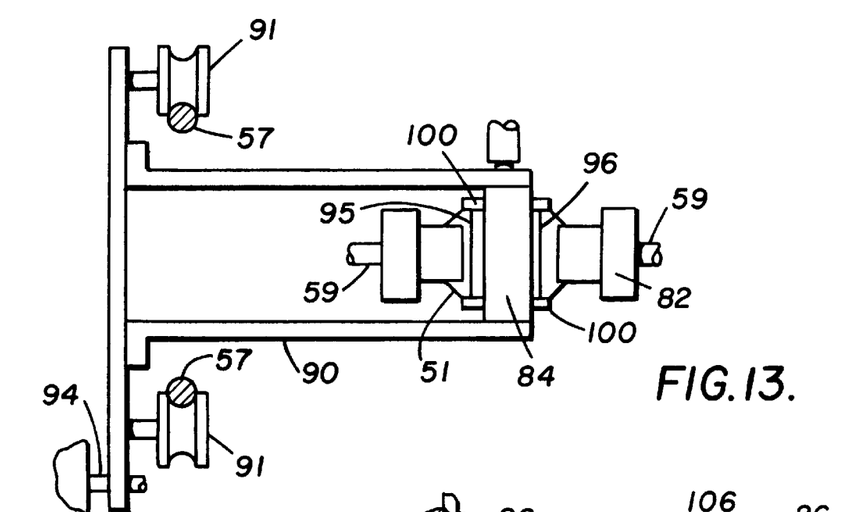
FIG. 13 is a plan view of a carriage which supports the holding manifold.

The holding manifold 84 is in the form of a hollow block (FIG. 9) having on opposite sides apertured walls 88 and 89 through which air can be passed into or out of the manifold. The holding manifold 84 is carried by a carriage 90 (FIG. 13) which is provided with rollers 91 which roll on the guide rods 57. For clarity, the carriage 90 is not shown in the starting position (FIG. 6) but, in this position, the carriage 90 rests on the carriage 52. When the cycle begins and the carriage 52 begins to move downward, the carriage 90 moves downward with it until the carriage 90 engages and is stopped by a stop 94 (FIG. 13) mounted above the base 46. The carriage 52 continues downward to complete the cycle. By adjusting the position of the stop 94, the lengths of the strips applied to each device can be adjusted, as will be seen below.

Figures 8, 9, 10, 11:
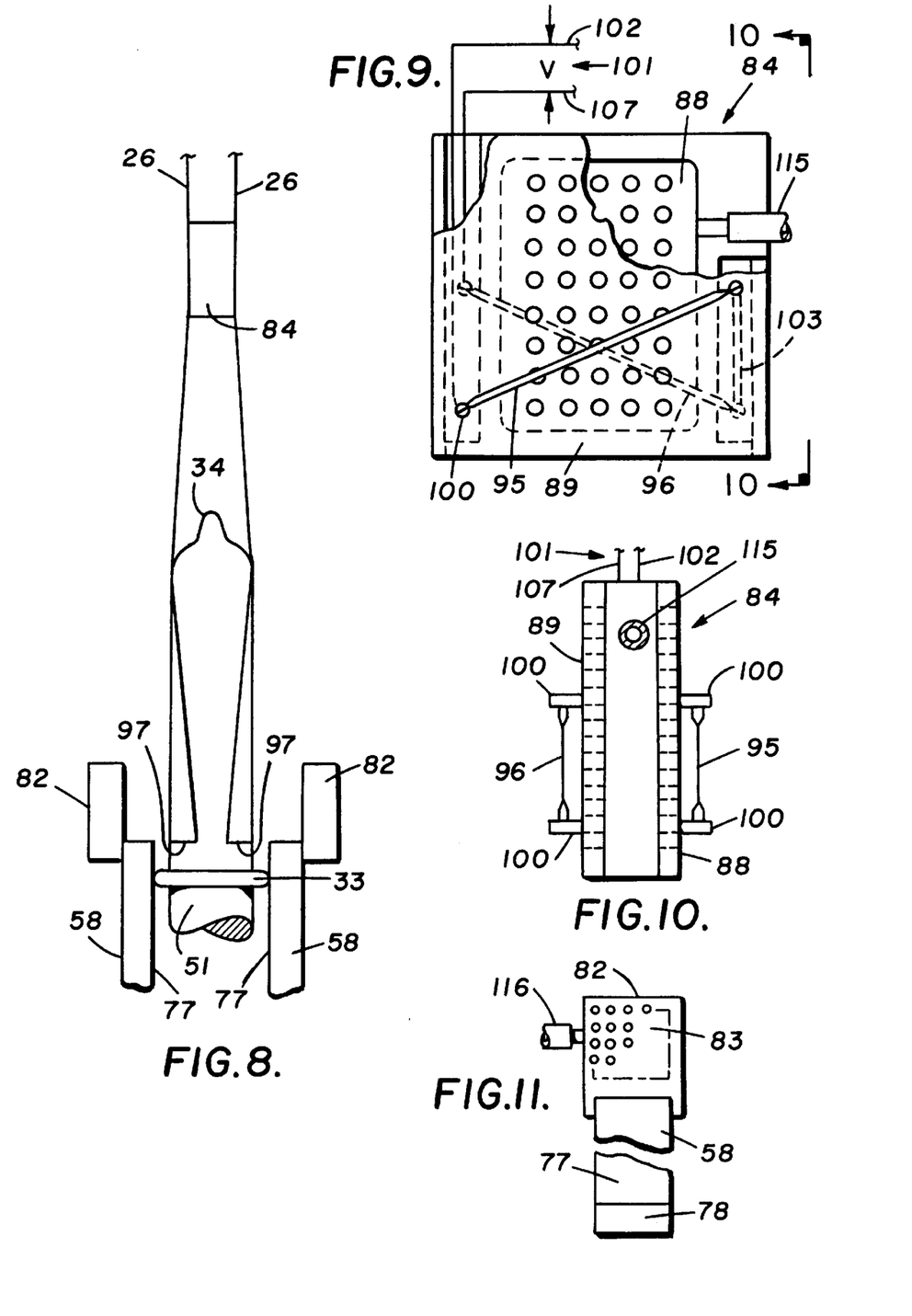
FIG. 8 is a schematic view of the apparatus of FIG. 6 showing the positioning of the apparatus in a second position at the midpoint of a cycle of operation.
FIG. 9 is an enlarged, fragmentary front view of a holding manifold which holds the strips during the second half of a cycle of operation, showing apertured surfaces through which air is drawn to hold the strips and spans of resistance wire which severs the strips.
FIG. 10 is a side view of the holding manifold taken on line 10—10 of FIG. 9 showing the spans of resistance wire which cut the strips at the end of the first half of a cycle of operation.
FIG. 11 is a front view, substantially reduced in size, of one of the condom rolling elements showing the apertured face of a feed manifold which holds the ends of the strips, during the first half of a cycle of operation, to carry the strips into position to be rolled with the condom during the second half of a cycle of operation.

The strips 26 are preferably cut from continuous strips, with the cutting being done at the holding manifold 84. The holding manifold 84 is provided with a pair of spans 95 and 96 of resistance wire positioned on opposite sides of the manifold as shown in FIGS. 9 and 10, the spans 95 and 96 being connected between conductive posts 100. Power from a supply 101 is fed through a line 102 to the first post 100; then through the span 95 to the second post 100; then through a line 103 to the third post 100; then through the span 96 to the fourth post 100; and then through a line 107 back to the other side of the power supply 101. By operating the spans 95 and 96 at a temperature somewhere below red hot, the thermoplastic strips will be instantly severed by cuts which are as sharp as cuts made by scissors. Since the strips 26 are cut at the holding manifold 84, it can be seen that adjusting the position of the stop 94 will adjust the lengths of the strips cut from continuous strips fed to the machine.

The apparatus shown in FIGS. 9 and 10 severs the strips on the bias (the cuts are not perpendicular to the length of the strips) while the strips shown In FIG. 8 are cut along lines perpendicular to the length of the strips. Either way is acceptable but cutting the strips on the bias is preferred for the reason that if the rolling of the condom catches the point formed by the cut the strip cannot escape. By "bias cut" is meant a cut which is more than 30° from a cut perpendicular to the length of the strip.

Figure 7:
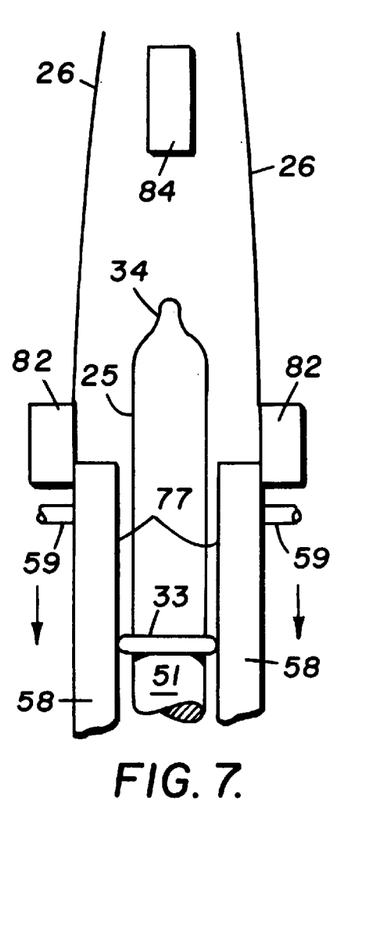
FIG. 7 is a schematic view of the apparatus of FIG. 6 showing the positioning of the apparatus at a point near the midpoint of the first half of a cycle of operation.

FIG. 7 shows the apparatus at a point during the first half cycle of operation. The holding manifold 84 has been stopped by engagement with the stop 94 (FIG. 13) and the rolling elements 58 continue to move downward, unrolling the condom 25 onto the form 51. A negative air pressure applied to the feed manifolds 82 holds the ends of the strips 26 so that they are pulled downward with the rolling elements 58. A positive air pressure applied to the holding manifold 84 keeps the strips 26 away from the heated spans 95 and 96 during this phase of operation.

FIG. 8 shows the apparatus in a second position at the end of the first half of the operating cycle. At this point, the rolling elements 58 have stopped. Valves (described below) have been actuated to apply a negative air pressure to the holding manifold 84 and a positive air pressure to the feed manifolds 82. The negative air pressure draws air into the holding manifold 84 through the apertured walls 88 and 89 to pull the strips 26 into contact with these walls to hold the strips. As the strips 26 move toward the apertured walls 88 and 89 they touch the resistance wire spans 95 and 96 and are instantly severed.

The positive air pressure applied to the feed manifolds 82 causes air to flow out of these manifolds through the apertured faces 83 to flatten the ends of the strips 26 against the condom 25 as shown in FIG. 8. When the preferred wider strips 26 (as described above) are used, it is critical that the ends of the strips be held in a flattened contact with the condom 25 on the form 51 as the rolling of the condom begins. By "flattened" we do not mean that the ends of the strips are held in a flat plane. Instead, we mean that the leading edges of the ends of the strips are in contact with the condom 25 as best shown in FIG. 8. The term "leading edge" refers to an edge 97 (FIG. 8) extending transversely across the strip and not to the two edges extending longitudinally along the length of the strips on opposite sides of the strip. By "generally flattened" contact we mean that, when the leading edge 97 is generally perpendicular to the length of the strip, at least one half of the length of the leading edge 97 of the strip is in contact with the condom. Preferably, at least 75% of the leading edge 97 of each strip 26 will be touching the condom when rolling of the condom begins. If the strip is cut on the bias such that the strip ends in a point, "generally flattened" contact means that at least one third of the leading edge 97, including the point, is in contact with the condom. This flattened contact, which is maintained at least until the ends of the strips are caught by the rolling of the condom, insures that the ends of the strips are not lost.

The preferred way of holding the strips 26 in flattened contact with the condom 25 is to use streams of air directed against the ends of the strips. In the apparatus shown, this is accomplished by the streams of air flowing from the feed manifolds 82. An alternate way of holding the ends of the strips 26 in place is to use a surface tension fluid or agent positioned between the condom and the ends of the strips, with the surface tension of the agent holding the strips in place. Preferably, the surface tension agent is a lubricant which is compatible with the condom.

Figure 14:
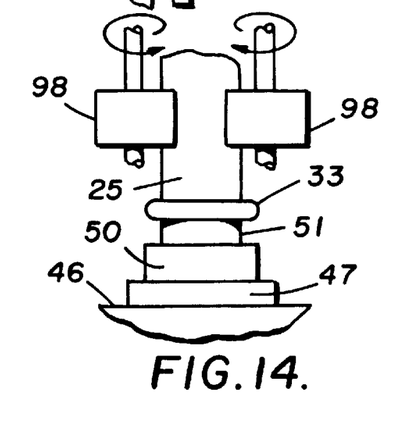
FIG. 14 is a schematic, fragmentary side view showing apparatus for applying a surface tension agent to the condom for holding the ends of the strips in contact with the condom for rolling.
Figure 15:
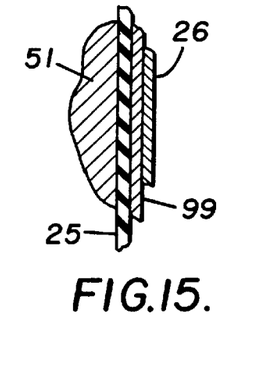
FIG. 15 is an enlarged, fragmentary cross sectional view showing how the surface tension agent holds the ends of the strips in contact with the condom for rolling.

FIG. 14 schematically shows the application of a surface tension agent to the condom for holding the strips 26 in place for rolling. The condom 25, positioned in unrolled condition on the form 51, is carried by the conveyor 47 past a station where a pair of rotating brushes 98 apply the surface tension agent 99 (FIG. 14) to the condom. The conveyor 47 then carries the condom past a second station where the strips are fed into position on opposite sides of the condom. When the ends of the strips 26 are brought into contact with the agent 99 the surface tension of the agent will hold the ends of the strips in place as shown in FIG. 15. The condom and strips can then be rolled at a third station.

If a surface tension agent is used to hold the strips 26 in place it is preferred that each strip be held in place by a narrow strip of the surface tension agent extending along the condom to the closed end thereof to hold a major portion of the condom. Care should be taken to not apply too much lubricant to the condom, since this can make the condom more difficult to roll. It should be understood that the surface tension agent can be applied to the strips rather than the condom. In either case, the surface tension agent should be positioned to contact both the condom and the strips, as shown in FIG. 15. The surface tension agent may be a sticky liquid or have a surface tension which will hold the strips in place. Water can be used but it is preferred to use a lubricant which is compatible with condoms. Such lubricants are well known.

Figure 16:
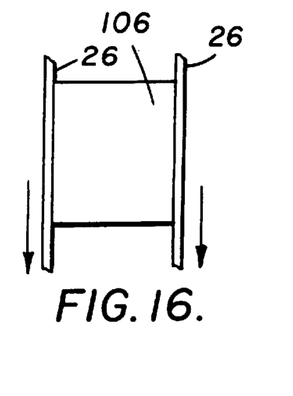
FIG. 16 is a fragmentary schematic side view showing the manner in which an electrostatic charge is applied to the strips to hold the strip ends in contact with the condom.

A second alternate way of holding the strips in place is to use an electrostatic attraction between the condom and the strips. This method is more difficult to control but it has been found that such an electrostatic attraction tenaciously holds the strips against the condom FIG. 16 schematically shows apparatus for electrostatically charging the strips 26. As the strips 26 are fed toward the location where the condom and strips are to be assembled, they pass over a device 106 of a known type which electrostatically charges the strips so that they will adhere to the condom by electrostatic attraction. If the device 106 is electronic in nature it can be turned on and off as the strips pass to charge only the ends of the strips.

The carriage 52 is then moved upward toward the first position to carry out the second half of a cycle of operation The rolling surfaces 77 in contact with the ring 33 of the condom 25 apply forces to the ring to roll the condom and the strips. When the rolling elements 58 reach the position shown in FIG. 6 the condom 25 will be left positioned on the top of the form 51, with the strips 26 rolled into it on opposite sides. The assembly of the condom and strips is now complete. While the reservoir 34 of the condom 25 is shown in a non-inverted configuration in FIGS. 6–8 it is preferred that the form 51 have a recess (not shown) and that a negative air pressure be applied to this recess at some point in the assembly of the condom and strips to invert the reservoir. The ribs 38 and 39 serve to maintain the reservoir in this inverted configuration during the remainder of the processing and packaging.

Figure 17:
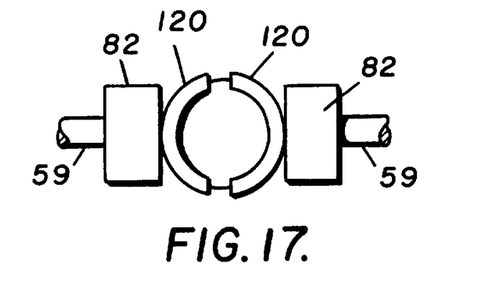
FIG. 17 is a fragmentary plan view of a preferred embodiment of the rolling elements where the rolling elements are semi-cylindrical in configuration.
Figure 18:
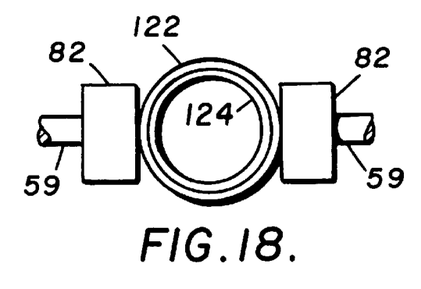
FIG. 18 is a plan view of a third embodiment of the rolling elements where the rolling elements are in the form of a single tube with a resilient inner lining.

The preferred configuration for the rolling elements is shown in FIG. 17, where rolling elements 120 are semi-cylindrical in configuration. This configuration provides for a greater contact between the rolling elements and the condom ring 33 for better rolling of the condom. Another embodiment is shown in FIG. 18 where the rolling elements are combined into a single tube 122 with a resilient liner 124. Preferably, the rolling elements 120 and 122/124 form tapered bores which have a diameter at any point equal to the diameter of the condom ring 33 at that point.

The Control System

Figures 19, 20:
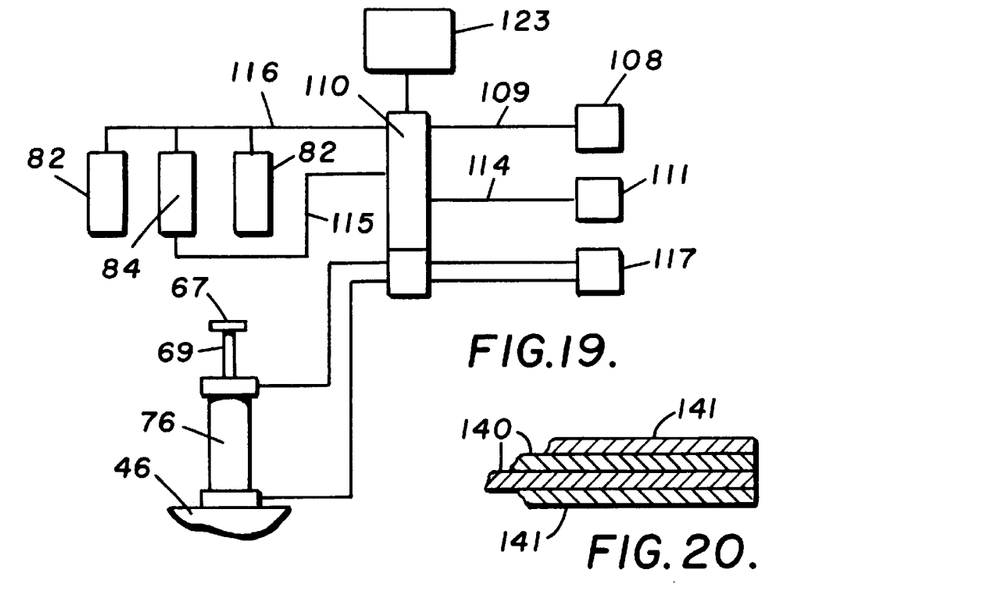
FIG. 19 is a schematic view of the system which drives and controls the apparatus used to assemble the device.
FIG. 20 is a fragmentary view, greatly enlarged, showing the two laminated layers which make up each of the two sheets used to package the device.

FIG. 19 is a schematic view of a system for controlling the apparatus described above, showing the air supply and control system. A supply 108 of air at a positive pressure (above atmospheric pressure) is connected by a line 109 to a valve 110 of a known type while a supply 111 of air at a negative pressure (below atmospheric pressure) is connected by a line 114 to the valve 110. The valve 110 is connected to the holding manifold 84 and the feed manifolds 82 by lines 115 and 116, respectively.

The valve 110 is such that air at a negative pressure is applied to the feed manifolds 82 at the same time that air at a positive pressure is applied to the holding manifold 84 and vice versa. Except for the instantaneous change from one pressure to the other, air at a negative pressure will always by supplied to either the feed manifolds 82 or the holding manifold 84 and air at a positive pressure to the other. Thus, the ends of the strips 26 are always held (except for the instantaneous change from one pressure to the other) by either the feed manifolds 82 or the holding manifold 84, so that the ends of the strips are always under control.

The valve 110 also controls the flow of a fluid (air or hydraulic fluid) from a source 117 to the fluid cylinder 76 mounted on the base 46 (FIG. 19) and having the piston rod 69 connected to the bracket 67 (FIGS. 12 and 19) secured to the carriage 52 such that operation of the cylinder 76 raises or lowers the carriage to carry the rolling elements 58 up and down.

The valve 110 is actuated by a controller 123 of a known type. For example, the valve 10 may be a bank of valves and the controller 123 may be a motor which drives cams (not shown) to actuate the valves. Or, the controller may sense the position of the carriage 52 and actuate the valve 110 (or bank of valves) in response to the position of the carriage 52. The primary purpose of the control system shown in FIG. 19 is to operate the various parts of the apparatus in timed sequence.

Packaging The Device

Packaging this device presents problems that do not exist in the packaging of conventional condoms. One of the problems results from the necessity of providing slack in the strips 26 as packaged so that the condom can be pulled out of the package as shown in FIG. 2 without premature unrolling. If the condom prematurely unrolls even a slight amount it can easily become tangled to the point where it must be discarded. This problem is solved by providing slack in the strips as described below.

Figure 21:
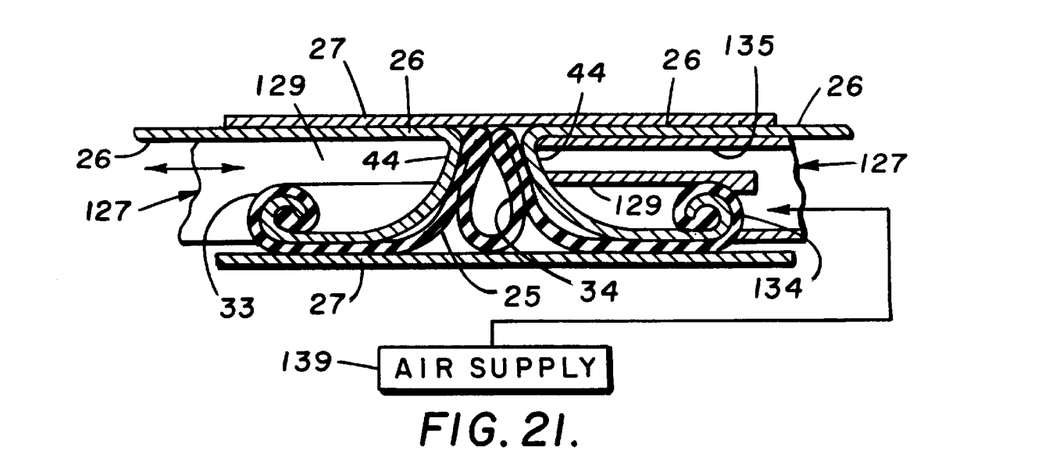
FIG. 21 is an enlarged side view showing the manner in which a pair of fingers are used to move intermediate portions of the strips toward each other and into contact with the condom to provide slack in the strips when the package is opened.
Figure 22:
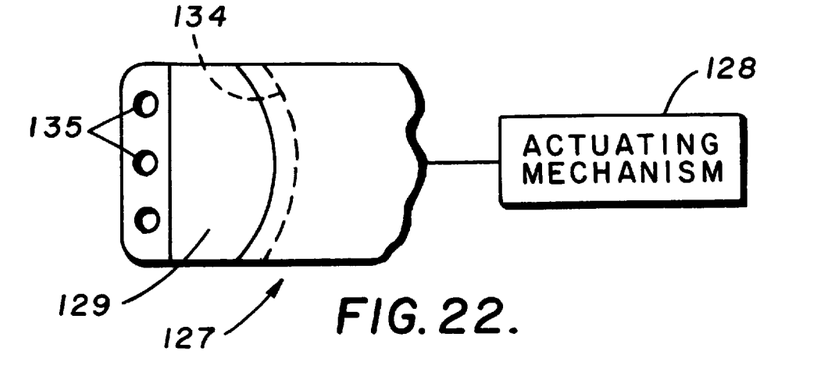
FIG. 22 is a fragmentary view of the bottom of one of the fingers shown in FIG. 21 showing that part of the finger which engages the periphery of the condom ring to center the condom.
Figure 23:
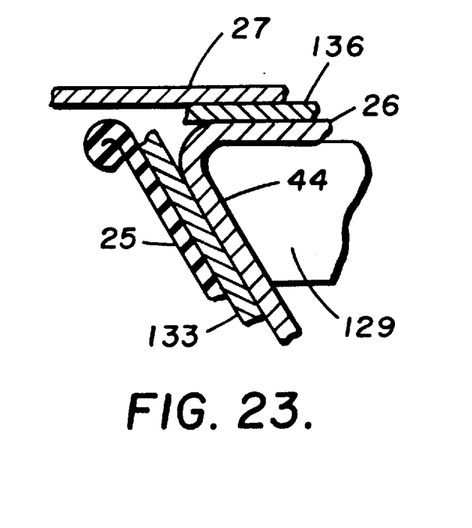
FIG. 23 is an enlarged fragmentary side view of one of the fingers showing the manner in which the finger pushes intermediate portions of the strips into contact with the lubricant on the condom to provide slack in the strips when the device is used.

A preferred way of providing slack in the strips 26 is to place the condom 25 on the bottom packaging sheet 27 with the strips 26 extending away from the condom in opposite directions. A pair of fingers 127 (refer to FIGS. 21–23) are then moved toward each other by an actuating mechanism 128 (FIG. 22). The fingers 127 are each provided with a projecting portion 129 positioned to engage the intermediate portions 44 of the strips 26 and move them inward past the condom ring 33 as best shown in FIG. 21. The actuating mechanism 128 may be a small cylinder (not shown).

In moving inward toward each other, the projecting portions 129 carry the intermediate portions 44 of the strips toward each other and into contact with a layer of lubricant 133 or a surface tension agent (FIG. 23) on the condom 25. As the fingers 127 are moved toward each other, surfaces 134 (FIGS. 21 and 22) engage the ring of the condom 25 to hold the condom in a centered position. After the fingers 127 are moved to the positions shown in FIGS. 21 and 23, the actuating mechanism 128 then withdraws the fingers 127. The surface tension of the lubricant 133 holds the intermediate portions 44 of the strips in the positions shown in FIG. 21 as the fingers 127 are withdrawn.

The lubricant can be placed at other locations to retain the strips in the positions shown in FIG. 21 as the fingers 127 are withdrawn. For example, the lubricant may be placed on either the strips or that packaging sheet 27 which will contact the strips when the sheets 27 are moved into contact with the device so that it will be in contact with both the strip 26 and the sheet 27. Reference numeral 136 in FIG. 23 indicates a lubricant or surface tension agent so positioned.

To insure that the strips 26 and the condom 25 remain in the position shown in FIG. 21 as the fingers are withdrawn, the fingers 127 may be provided with a passageway 135 through which air from a supply 139 (FIG. 21) can impinge on the strips and the condom The withdrawal of the fingers 127 positions the ends of the strips 26 to extend away from each other as shown in FIG. 21. The top packaging sheet 27 is then placed over the condom and the packaging sheets are sealed to each other as described below.

Preferably, the packaging sheets 27 are each made up of two layers of material laminated together. FIG. 20 is a greatly enlarged, fragmentary view showing the two layers making up each sheet 27. Each sheet is made up of an inner layer 140 and an outer layer 141, with the inner layers 140 being in contact with each other in the final package. The outer layer 141 may be a layer of a material such as paper, foil, cellophane, polyethylene terephthalate, etc. The inner layer 140 is preferably a sheet of polyethylene. The sheets are secured together to form the package by placing the inner layers in contact with each other and then applying heat and pressure to the zone 32 to be sealed (FIG. 25).

Since heat and pressure will be applied to the zone 32 during the package sealing step, care must be taken to insure that the strips 26 are not severed or seriously weakened by melting at the inner edge of the zone 32. By "seriously weakened" we mean a weakening of the strips to the point where one will occasionally break when tension is applied to pull the condom 25 out of the package or onto the user's penis. If either of the strips breaks, the device is rendered inoperative for its intended purpose.

The heat to seal the package is applied by a pair of heated dies 144 between which the sheets 27 are sandwiched (FIGS. 24 and 25), with the configuration of the dies conforming to the shape of the zone 32 to be sealed. The amount of heat input to the sheets 27 will be determined by the temperature of the dies, the pressure applied to the sheets 27 by the dies 144 and the length of time that the dies are in contact with the sheets. By controlling these factors the package can be completely sealed without seriously weakening the strips 26.

Preferably, a differential heating will be applied to inner and outer portions of the zone 32 at the locations of the strips 26. This is accomplished by providing dies which have the cross sectional configuration shown in FIG. 25, where the die is divided into subzones A and B. This view shows the intersection of the die faces with a plane longitudinal to the strips and perpendicular to the die faces. From this it can be seen that in the subzone A these intersections are parallel lines. In the subzone B the intersections are a pair of lines which extend inwardly (toward the center of the package) and are divergent. Preferably, the die faces in the subzone B have a configuration such that the intersection lines are arcuate and are so positioned that the parallel intersection lines in the subzone A are each tangent to one of the arcuate lines as shown in FIG. 25.

In the subzone A the dies apply the maximum pressure to the sheets 27 and in the subzone B the surfaces of the dies recede from the sheets 27, as shown in FIG. 25. In the subzone A the amount of heat input to the sheets preferably exceeds the melt heat input requirements of both the strip 26 and the inner layers 140 to melt them and thoroughly seal that part of the zone 32. At some point in the subzone B, because the surfaces of the dies recede from the sheets 27, the amount of heat input to the strips 26 will be less than the melt heat input requirement of the strips 26 while the amount of heat applied to the inner layers will be above the melt heat input requirement of the inner layers 140 to firmly adhere the inner layers 140 to the strips 26 without melting the strips. It can readily be seen that heat applied to the strips 26 must pass through the inner layers 140.

By "melt heat input requirement" is meant the amount of heat which must be input to the material to melt it. The melt heat input requirement of a material will be determined by the melting point (temperature) of the material and, for a given area of the material, the thickness of the material. For example, a one square centimeter of film 0.088 mm thick will have a melt heat input requirement approximately six times that of a film of the same material only 0.013 mm thick.

Figure 24:
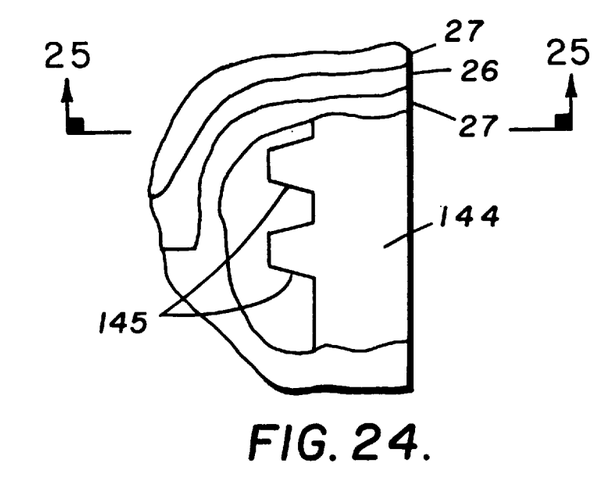
FIG. 24 is an enlarged fragmentary view showing the configuration of dies used to seal the packaging sheets to each other around the periphery thereof.

More preferably, the dies will be provided with projections 145 as shown in FIGS. 24 and 25 to insure that the inner layers 140 are securely attached to the strip 26 without damage to that part of the strip. While flat dies are shown, it should be understood that the same principles would apply to rotating dies where the peripheries of the dies apply heat and pressure to the zone 32. In this case, the inner surfaces of the dies in subzone B would recede from the sheets 27 as shown in FIG. 25 to apply a differential heating to the zone 32.

By sealing the package in this manner it is assured that the package is hermetically sealed without the risk of severing or severely weakening the strips 26 at the inner edge of the sealed zone 32.

What is claimed is:

1. A contraceptive device comprising a condom having an elongated tubular configuration with an open end and a closed end, said closed end having thereon a generally cylindrical reservoir, said reservoir having thereon a plurality of ribs positioned in an annular zone having extending axially along said reservoir, said ribs extending across the width of said annular zone and being so positioned that no annular band of said zone is free of ribs.

2. The device of claim 1 wherein the condom is provided with a plurality of second ribs positioned in a second annular zone on the closed end of the condom, said second zone having a width extending axially along the condom, said zones being so spaced from each other that there is an annular band of said condom between the zones which is free of ribs, said second ribs extending across the width of the second zone and being so positioned in said second zone that there is no annular band of said second zone which is free of ribs.

3. The process of assembling a contraceptive device made up of a pair of strips rolled into an elongated condom on opposite sides thereof, each of said strips having an end having a leading edge, comprising;
   a. placing the condom in unrolled condition on an elongated form,
   b. bringing the ends of the strips into generally flattened contact with the condom on the form and holding at least one third of said leading edges in contact with said condom, and
   c. rolling the condom and strips.

4. The process of claim 3 wherein the strips are moved into said generally flattened contact with the condom by means of streams of air directed against the ends of the strips.

5. The process of claim 3 wherein the strips are held in said generally flattened contact with the condom by means of an electrostatic attraction between said condom and said ends.

6. The process of claim 3 wherein the strips are held in generally flattened contact with the condom by means of a surface tension agent placed between the condom and said ends of said strips.

7. The process of claim 3 wherein at least 75% of the leading edge of the end of each strip is held in contact with said condom.

8. A process for assembling a contraceptive device made up of a rolled tubular condom lying in a plane and having an open end and a closed end, said device also having a pair of strips having first ends rolled into the condom on opposite sides thereof, said strips each having an intermediate portion and a free second end, said device also having first and second packaging sheets positioned on opposite sides of said plane to sandwich the condom therebetween, said first packaging sheet having a side facing the open end of the condom, said second sheet having a side facing the closed end of the condom, comprising
   a. placing a surface tension agent on said device,
   b. moving the intermediate portions of the strips toward each other, said surface tension agent being placed on the device in a location to contact the intermediate portions of the strips when the strips are moved toward each other,
   c. positioning the second ends of the strips to extend away from said intermediate portions in opposite directions,
   d. bringing the packaging sheets into contact with each other on opposite sides of the condom, and
   e. sealing the packaging sheets to each other around the edges thereof.

9. The process of 8 wherein the surface tension agent is placed on the intermediate portions of the strips to be contacted by the second sheet when said second sheet contacts the strips.

10. The process of claim 8 wherein the surface tension agent is placed on the closed end of the condom and the intermediate portions of the strips are moved into contact with the surface tension agent on the condom.

11. The process of claim 8 wherein the surface tension agent is placed on said side of said second sheet in a position to contact the intermediate portions of the strips when said sheet is brought into contact with said intermediate portions.

12. The process of claim 8 wherein the moving of said intermediate portions of the strips toward each other is done by a pair of fingers moved toward each other from opposite sides of the condom.

13. A process for assembling a contraceptive device made up of a rolled tubular condom having a pair of strips having first ends rolled into the condom on opposite sides thereof and a pair of packaging sheets positioned to sandwich the condom therebetween, said sheets each being made up of inner and outer layers laminated together, said inner layers facing each other and being made of a thermoplastic material having a first melt heat input requirement, said strips being made of a thermoplastic material having a second melt heat input requirement, comprising
   a. positioning the condom between the packaging sheets with said inner layers in contact with each other around the periphery of the sheets and said strips extending away from each other toward opposite edges of the packaging sheets, and
   b. applying heat and pressure to a zone extending around the periphery of the sheets to seal said sheets to each other and to the strips, said zone comprising first and second subzones, said first subzone extending inwardly from the edges of the sheets and said second subzone extending inwardly from said first subzone, the amount of heat applied to the first subzone being sufficient to exceed both the first and second melt heat input requirements of said inner layers and said strips, the amount of heat applied to the second subzone being such that at a point in said second subzone the heat applied to the inner layers exceeds the first melt heat input requirement and the heat applied to the strips is less than said second melt heat input requirement.

14. The process of claim 13 wherein the pressure applied to said zone is greatest in the first subzone and decreases to a minimum in the second subzone.

15. Apparatus for assembling a contraceptive device made up of a pair of strips rolled into a tubular condom on opposite sides thereof and a pair of packaging sheets positioned to sandwich the condom therebetween, comprising
   a. a base,
   b. means on the base for supporting the condom in a working position with the strips extending from the condom in opposite directions,
   c. a pair of fingers positioned on opposite sides of the condom in said working position,
   d. means connected to the fingers for moving the fingers back and forth toward and away from each other, said fingers being so positioned that said fingers engage intermediate portions of the strips and move said intermediate portions into contact with the condom when the fingers are moved toward each other.

16. The apparatus of claim 15 wherein the fingers are provided with passageways for directing streams of air against said intermediate portions of the strips to separate said intermediate portions from the fingers when said fingers are moved away from each other.

17. The apparatus of claim 15 wherein the fingers are each provided with a surface positioned to engage the periphery of the condom to center said condom in said working position.

18. Apparatus for forming a package for a contraceptive device made up of a rolled condom having a pair of thermoplastic strips having first ends rolled into the condom and free second ends extending away from the condom in opposite directions with said condom and said strips being positioned between a pair of packaging sheets having thermoplastic layers in contact with each other around the periphery thereof, comprising a pair of dies having opposing faces to be positioned on opposite sides of the packaging sheets for applying heat and pressure to the sheets to melt the thermoplastic layers around the periphery thereof to seal the packaging sheets to each other to form said package, said opposing faces at the locations of the strips being made up of a first subzone extending inwardly from the edges of the faces and a second subzone extending inwardly from the first subzone, said faces being so configured that the intersections of said faces in said first subzone with a plane longitudinal to the strips and perpendicular to said faces form a pair of parallel first lines, said faces also being so configured that that the intersections of said faces in said second subzone with said plane form a pair of diverging second lines each extending from one of the parallel first lines.

19. The apparatus of claim 18 wherein the second lines are arcuate lines so positioned that each of said parallel first lines is tangent to one of said arcuate lines.

20. A process for assembling a contraceptive device made up of a condom having a pair of strips rolled into the condom on opposite sides thereof, said condom having an axis, a closed end, an open end and a ring extending around said open end, comprising
   a. placing the condom on an elongated form having a free end such that the free end of the form is in the closed end of the condom and the open end of the condom is spaced from the free end of the form,
   b. bringing free ends of a pair of strips into contact with the condom on opposite sides thereof adjacent to the ring on the open end of the condom,
   c. bringing an elongated rolling surface into contact with the ring on the condom, and
   d. moving the rolling surface along a path parallel to the axis of the form and in a direction toward the closed end of the condom to roll the condom and the strips.

21. The process of claim 20 wherein a pair of rolling surfaces are brought into contact with said ring on opposite sides of the condom and then moved along paths parallel to each other in a direction toward the closed end of the condom to roll the condom and strips.

22. The process of claim 21 wherein streams of air are directed onto the ends of the strips to hold said strips in contact with the condom as the rolling of the condom is begun.

23. The process of claim 21 wherein the condom is placed on the form by positioning the condom in rolled form on the free end of the form and then moving the rolling surfaces along parallel paths in directions toward the open end of the condom while maintaining said rolling surfaces in contact with the rolled portion of the condom to unroll said condom onto said form.

24. Apparatus for assembling a contraceptive device made up of an elongated tubular condom having a pair of strips rolled into the condom on opposite sides thereof, said condom having an open end and a closed end with a ring encircling the open end, comprising
   a. a base,
   b. an elongated form having first and second ends, said first end being free and said second end being attached to the base, said form having an axis,
   c. a pair of rolling elements positioned on opposite sides of the form and each having thereon a rolling surface, said elements being moveable between first and second positions in such a manner that when said elements are moved from said second position to said first position the rolling surfaces are carried along paths generally parallel to the axis of the form, said elements being so positioned that when the rolling surfaces are moved from the second position to the first position the rolling surfaces contact the ring on the condom to roll the condom, and
   d. means on the base for moving the rolling elements.

25. The apparatus of claim 24 wherein the rolling elements are provided with means for holding ends of a pair of strips to pull said strips into position adjacent to and on opposite sides of the form when the rolling elements are moved from the first position toward the second position.

26. The apparatus of claim 25 wherein the strip holding means is a pair of feed manifolds mounted on the rolling elements, said manifolds having facing apertured surfaces through which air can flow into and out of the manifolds.

27. The apparatus of claim 26 wherein the apparatus further comprises valve means connected to the feed and holding manifolds and further comprises means for operating the valve means in timed relationship with movement of the rolling elements such that, when air supplies of positive and negative pressures are connected to said valve means, as the rolling elements are being moved from the first position to the second position negative air pressure is applied to the feed manifolds and positive air pressure is applied to the holding manifold and as the rolling elements are being moved from the second position to the first position positive air pressure is applied to the feed manifolds and negative air pressure is applied to the holding manifold.

28. The apparatus of claim 24 wherein the strips are continuous and a second means for holding strips in position is positioned on said axis at a location spaced from the free end of the form, said apparatus also having strip severing means positioned at said location for cutting the strips.

29. The apparatus of claim 28 wherein the second holding means is a holding manifold having on opposite sides thereof a pair of apertured walls through which air can flow into and out of said manifold, said second manifold being positioned between the first manifolds when the rolling elements are in said first position.

30. The apparatus of claim 28 wherein the strip severing means comprises a pair of spans of resistance wire positioned on opposite sides of the holding manifold.

31. The apparatus of claim 24 wherein the rolling elements are semi-cylindrical in transverse cross section.

32. The apparatus of claim 31 wherein interior faces of the rolling elements face each other and form a bore having a diameter which varies along the length of said rolling elements to accommodate changes in the diameter of the condom ring as said condom is being rolled.

* * * * *